United States Patent [19]

Kallok et al.

[11] 4,355,646

[45] Oct. 26, 1982

[54] TRANSVENOUS DEFIBRILLATING LEAD

[75] Inventors: Michael J. Kallok, New Brighton; John D. Doring, Spring Lake Park, both of Minn.

[73] Assignee: Medtronic, Inc., Minneapolis, Minn.

[21] Appl. No.: 210,656

[22] Filed: Nov. 26, 1980

[51] Int. Cl.³ .............................................. A61N 1/04
[52] U.S. Cl. ................................ 128/786; 128/419 D
[58] Field of Search ............... 128/419 D, 419 P, 784, 128/785, 786

[56] References Cited

U.S. PATENT DOCUMENTS

| | | | |
|---|---|---|---|
| 3,333,045 | 7/1967 | Fisher et al. | 128/419 P |
| 3,416,533 | 12/1968 | Fisher et al. | 128/404 |
| 3,572,344 | 3/1971 | Bolduc | 128/418 |
| 3,857,398 | 12/1974 | Rubin | 128/419 D |
| 3,942,536 | 3/1976 | Mirowski et al. | 128/786 |
| 4,033,357 | 7/1977 | Helland et al. | 128/418 |

OTHER PUBLICATIONS

"Optimal Spacing of Right Ventricular Bipolar Catheter Electrodes for Detecting Cardiac Pumping by an Automatic Implantable Defibrillator", by W. A. Tacker, Jr., et al., Medical Instrumentation, vol. 14, No. 1, Jan.-Feb. 1980.

Medtronic® Transvenous, Tined, Ventricular Leads Models 6971 and 6972 -Jul. 1979.

*Primary Examiner*—William E. Kamm
*Attorney, Agent, or Firm*—John L. Rooney; Joseph F. Breimayer; Robert C. Beck

[57] ABSTRACT

A lead having multiple electrodes which is transvenously implanted for use in standby defibrillation of patients having a high risk of ventricular fibrillation. The lead employs four electrodes. The two distal electrodes have a spacing for optimal measurement of impedance changes due to mechanical contractions. This impedance measurement is used for mechanical sensing of normal cardiac activity. The electrode at the very distal tip terminates in a hemispherical shape. Two proximal electrodes are closely spaced and located at a distance from the two distal electrodes which ensures their placement within the superior vena cava whenever the distal electrodes are placed within the right ventricular apex. The body of the lead uses drawn brazed strand conductors wound triaxially for maximum flexibility, minimum cross-sectional area and the required high current carrying capability. At the proximal end of the lead, three connectors are used to electrically couple the lead to an implantable pulse generator. The two distal electrodes are electrically separated and each terminates in a separate proximal connector. The two proximal electrodes are electrically coupled to a single proximal connector. A stylet is employed to aid in implantation.

5 Claims, 3 Drawing Figures

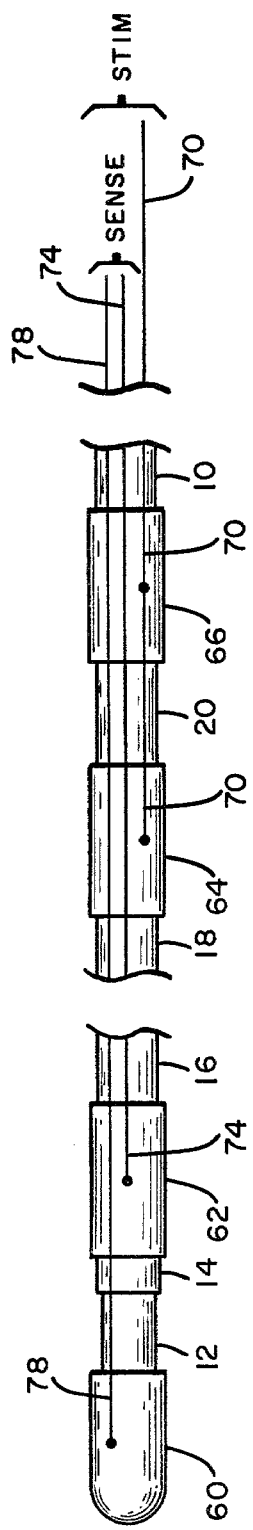
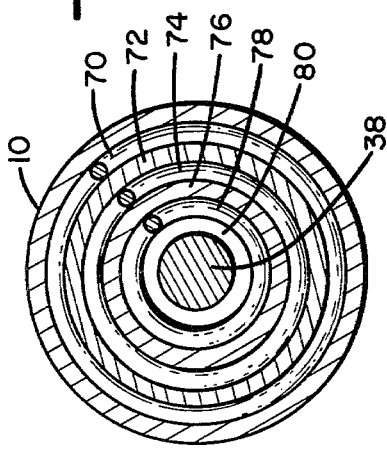

TRANSVENOUS DEFIBRILLATING LEAD

BACKGROUND OF THE INVENTION

1. Field of the Invention

The present invention relates generally to implantable medical devices and more specifically relates to electrodes for chronic implantation for electrical defibrillation.

2. Description of the Prior Art

Research to provide an automatic implantable standby defibrillator has been in progress for over ten years. The very earliest attempts employed paddle-style electrodes which simulated the paddle electrodes used in external defibrillators. Because of the ease of implantation, efforts very quickly shifted to the use of transvenous electrodes. Much effort was expended in attempting to provide a practical transvenous defibrillator. The problems to be solved were: choice of a sensing technique or techniques; the placement of the electrodes; and the minimization of defibrillating energy thresholds.

Mirowski et al in U.S. Pat. No. 3,942,536 teach an early defibrillation technique using a transvenous defibrillating lead. The sensing scheme used employs an implantable pressure transducer which is implanted with the electrodes but functions totally independent of them. Defibrillation is determined by a loss of right ventricular pressure. Mirowski et al employ multiple electrodes inserted at the apex of the right ventricle and multiple electrodes to be positioned within the superior vena cava.

Heilman et al, in U.S. Pat. No. 4,030,509, teach the use of electrodes which are placed externally. The literature contains substantial information about why this scheme is superior. Basically it was found by Heilman et al and others in the area that the energy required for cardioversion was substantially less by using external electrodes. U.S. Pat. No. 4,161,952 issued to Kinney et al is a further example of the art of continually more sophisticated external electrodes having reduced energy thresholds.

Work has been progressing in the art of transvenous defibrillator leads but progress has been relatively slow. To be provided is a lead having an optimal sensing scheme. Normally this assumes the employment of more than one sensing technique. It is felt that electrical sensing of electrocardiogram information alone is insufficient since it describes only electrical activity of the heart muscle and does not describe the actual mechanical activity. Because of the difficulty in supplying reliable mechanical sensors for chronic implantation the sensing problem has been a major deterrent in the development of a transvenous lead.

Currently the most favored technique for sensing of mechanical contractions of the heart is to use an impedance measuring technique. This technique uses two electrodes which are electrically isolated but which are both located within the right ventricle. A small radio frequency current is passed between the two electrodes and the impedance of that transmission is monitored. As the heart contracts the amount of blood within the ventricle decreases substantially resulting in an increase in the impedance monitored. In a paper by W. A. Tacker, Jr., entitled "Optimal Spacing of Right Ventricular Bipolar Catheter Electrodes for Detecting Cardiac Pumping By an Automatic Implantable Defibrillator," published in *Medical Instrumentation*, Vol. XIV, No. 1, January–February, 1980, the technique for optimizing the spacing of the two impedance matching electrodes is discussed.

SUMMARY OF THE INVENTION

The present invention provides a transvenous defibrillation lead having electrically isolated distal electrodes which are used for impedance monitoring as taught by Tacker, Jr. et al. The electrodes at the distal end are spaced at an optimal 5 mm. Two electrically common electrodes are placed proximal within the superior vena cava. The electrode at the distal tip terminates in a hemispherical shape to reduce cardioverting thresholds.

Three mutually insulated conductors are required. A first conductor is connected to the distal electrode at the very tip of the lead. A second conductor is coupled to the second distal electrode. A third conductor is coupled to both of the electrodes located within the superior vena cava. To reduce cross-sectional area of the lead, the three conductors are arranged triaxially. The electrodes are fabricated from a body compatible material such as stainless steel, titanium or platinum alloy. To enable the conductors to carry the relatively high currents associated with defibrillation, drawn brazed strand wires having a silver core are used. To provide the required strength within the lead body the conductors are coiled in quadrafilar fashion. Polyurethane is used for the outer sheath to increase the ease of implantation and to further reduce the cross-sectional area.

BRIEF DESCRIPTION OF THE DRAWINGS

FIG. 2 is a cross-section of the lead showing the three mutually insulated conductors arranged in triaxial fashion.

FIG. 3 is a schematic diagram showing the electrical coupling of the four electrodes to the three conductors within the lead body.

DETAILED DESCRIPTION OF THE PREFERRED EMBODIMENT

Figure 1:
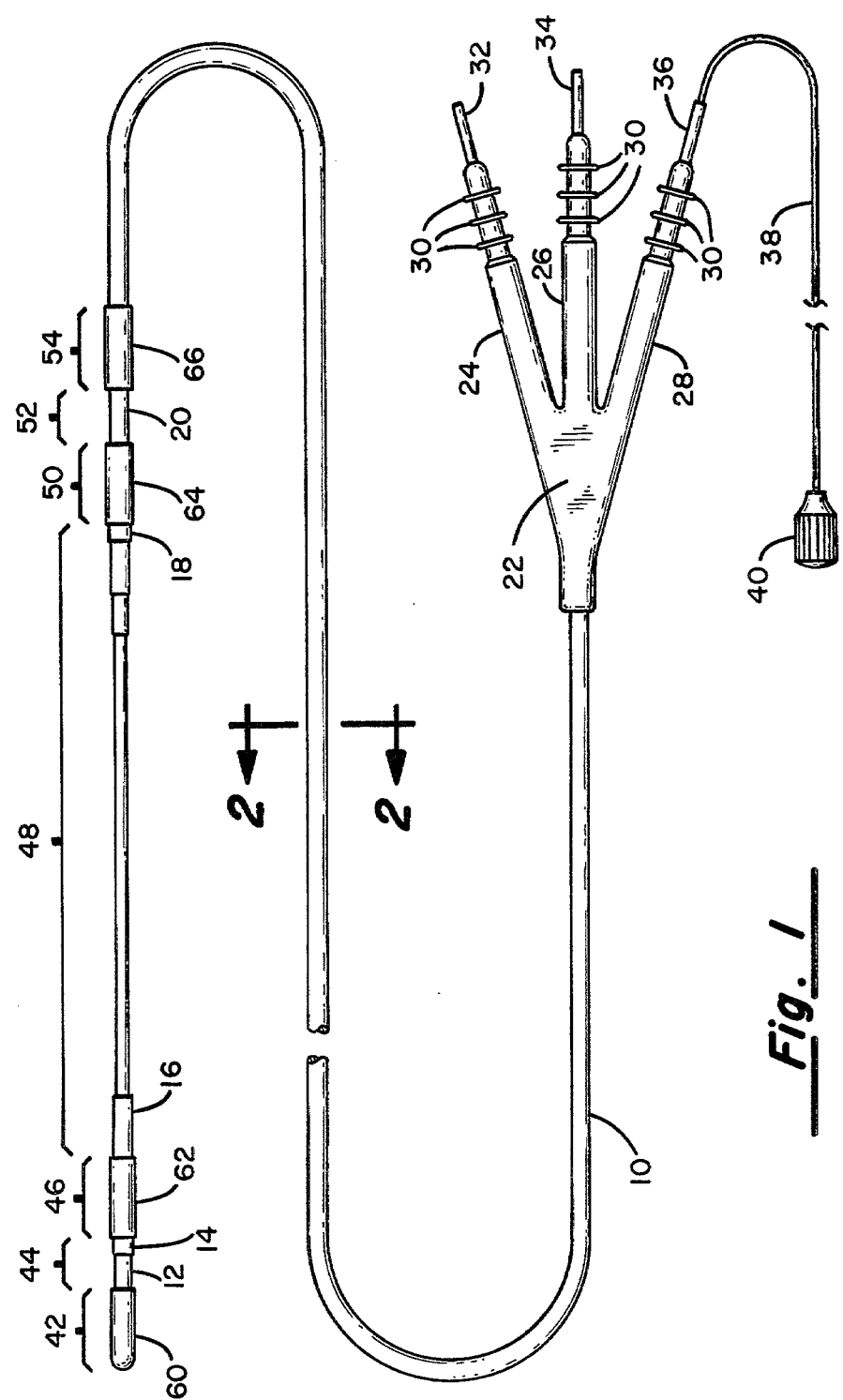
FIG. 1 is a plan view of a transvenous defibrillating lead employing the present invention.

The preferred embodiment of the present invention is described as employed within a lead built by the assignee of the present invention. This lead has undergone a number of tests which have resulted in optimization of the various dimensions described herein. Those of ordinary skill in the art will be able to appreciate that a number of these dimensions may be varied within the scope of the present invention whereas other aspects must be made in accordance with the teaching herein to properly practice the present invention.

FIG. 1 shows a transvenous defibrillating lead employing the present invention. The lead has four electrodes. Electrodes 60 and 62 are the distal electrodes which are positioned within the right ventricle. The proximal electrodes 64 and 66 are properly placed within the superior vena cava. Distal electrode 60 is most properly implanted in the apex of the right ventricle. As can be seen in the diagram the distal tip of electrode 60 is hemispherical in shape. This is extremely important to the proper establishment of current densities at relatively low energy thresholds. Electrode 62 is properly placed within the right ventricle also. The distance 44 between the proximal end of electrode 60 and the distal end of electrode 62 is properly placed at 5 mm.

Electrode 64 and electrode 66 are positioned within the superior vena cava as explained above. The distance between the proximal end of electrode 64 and the distal end of electrode 66 is also about 5 mm although this distance is not critical. Electrodes 60, 62, 64 and 66 all have an effective surface area of approximately 125 mm square. All four electrodes may be fabricated of any conductor which is essentially inert to body fluids. The preferred mode employs stainless steel; however, other materials such as titanium or a platinum alloy may be used. Electrodes 62, 64 and 66 are cylindrical in shape and are swaged onto the main body of the lead.

To properly position electrodes 64 and 66 within the superior vena cava when electrode 60 is located at the apex of the right ventricle, distance 48 is approximately 100 mm.

Each of the electrodes (i.e. electrodes 60, 62, 64 and 66) has a surface area of approximately 125 mm square. Each of the four electrodes is approximately 0.475 inches in length. Electrodes 62, 64 and 66 are cylindrical in shape. Electrode 60 is cylindrical with a hemispherical distal end. The main body of lead 10 is approximately 2.79 mm in diameter, it is covered with a urethane sheath. Connector 22 has three electrical connections, that is connector pins 24, 26 and 28. Each of the connector pins has three sealing rings marked reference number 30. The electrical terminals are 32, 34 and 36, respectively. Stylet wire 38, having stylet knob 40 at its distal end, may be inserted into terminal pin 36 and extended through lumen 80 until it reaches distal electrode 60. The stylet is used for guiding the lead during transvenous implantation.

FIG. 2 is a cross-section of the main lead body. One can see that outer sheath 10 protects the lead from the ingress of body fluids. Conductors 70, 74 and 78 are mounted triaxially within the lead. Each is a quadrafilar helical coil of drawn brazed strand (DBS½). To handle the current associated with defibrillation, the drawn brazed strand has an inner core of silver and is surrounded by a number of wires having substantially greater tensile strength such as alloy MP35N. The three conductors are mutually insulated by polyurethane sheaths 10, 72 and 76. Inner lumen 38 is used for insertion of stylet wire 38 to guide the lead during implantation.

FIG. 3 illustrates schematically the electrical connections of the various electrodes at the distal end of the lead. As can be seen, conductor 78 which is the inner conductor is electrically connected to electrode 60. (See also FIG. 2). Referring again to FIG. 3, it can be seen that electrical conductor 74, which is the middle conductor in the triaxial configuration, is connected electrically to electrode 62. The outer conductor which is conductor 78 is connected electrically to both electrode 64 and electrode 66. During sensing the pulse generator (not shown) measures the impedance change between electrodes 60 and 62 using conductors 70 and 74. During defibrillation, electrodes 60 and 64 are essentially connected together electrically at the pulse generator such that conductors 70 and 74 acquire the same potential.

Having thus described the preferred mode of the present invention, those of ordinary skill in the art will appreciate that certain of the design characteristics taught herein may be varied and still remain within the scope of the present invention.

What is claimed is:

1. A transvenous defibrillator lead for insertion into a right ventricle of a heart by way of a superior vena cava comprising:
   an insulated conductive lead body having a proximal end and a distal end, said conductive lead body comprising three mutually insulated conductors of drawn brazed strand arranged in a triaxial configuration and an outer sheath of polyurethane;
   an electrical connector at said proximal end;
   a first electrode having a distal tip with a hemispherical shape attached to said distal end of said insulated conductive lead body;
   a second electrode attached to said insulated conductive lead body at a distance from said first electrode wherein said first distance is sufficiently short that said second electrode is within said right ventricle when said first electrode is at an apex of said right ventricle;
   a third electrode attached to said insulated conductive lead body at a second distance from said first electrode wherein said second distance is such that said third electrode is within said superior vena cava when said first electrode is at said apex of said right ventricle; and
   a fourth electrode attached to said insulated conductive lead body at a third distance from said first electrode wherein said third distance is different from said second distance and wherein said fourth electrode is within said superior vena cava when said first electrode is at said apex of said right ventricle.

2. A transvenous defibrillator lead according to claim 1 wherein said first distance is 5 mm.

3. A transvenous defibrillator lead according to claim 2 wherein said insulated conductive lead body further comprises:
   an outer sheath of polyurethane.

4. A transvenous defibrillator lead comprising:
   an elongated first insulative sheath of polyurethane;
   a first coiled conductor of drawn brazed strand mounted within said first insulative sheath;
   a second insulative sheath of polyurethane mounted coaxially within said first coiled conductor;
   a second coiled conductor of drawn brazed strand mounted within said second insulative sheath;
   a third insulative sheath of urethane mounted coaxially within said second coiled conductor;
   a third coiled conductor of drawn brazed strand mounted within said third insulative sheath;
   a first electrode coupled to the distal end of said first coiled conductor;
   a second electrode coupled to the distal end of said second coiled conductor; and
   a third electrode coupled to the distal end of said third conductor.

5. A transvenous defibrillator lead according to claim 4 wherein said first, second and third coiled conductors are quadrafilar coils.

* * * * *

UNITED STATES PATENT AND TRADEMARK OFFICE
CERTIFICATE OF CORRECTION

PATENT NO. : 4,355,646
DATED : 26 October 1982
INVENTOR(S) : Michael J. Kallok et al It is certified that error appears in the above-identified patent and that said Letters Patent are hereby corrected as shown below:

Column 3,

Line 40, "DBS1/2)" should be --(DBS™)--;

Line 46, "38" should be --80--;

Line 51, "78" should be --70--;

Line 61, "70" should be --78--;

Line 62, "64" should be --62--;

Line 64, "70" should be --78--.

Signed and Sealed this

Fifth Day of February 1985

[SEAL]

Attest:

DONALD J. QUIGG

Attesting Officer     Acting Commissioner of Patents and Trademarks